United States Patent
Henrich et al.

(10) Patent No.: US 6,496,562 B1
(45) Date of Patent: Dec. 17, 2002

(54) ENERGY DISPERSION X-RAY FLUORESCENCE ANALYSIS OF CHEMICAL SUBTANCES

(75) Inventors: Alexander Henrich, Gross-Gerau (DE); Hans-Helmut Itzel, Ober-Ramstadt (DE); Peter Hoffmann, Darmstadt (DE); Hugo Ortner, Seeheim-Jugenheim (DE)

(73) Assignee: Merck Patentgesellschaft mit Beschrankter Haftung, Darmstadt (DE)

( * ) Notice: Subject to any disclaimer, the term of this patent is extended or adjusted under 35 U.S.C. 154(b) by 0 days.

(21) Appl. No.: 09/889,700
(22) PCT Filed: Jan. 7, 2000
(86) PCT No.: PCT/EP00/00070
§ 371 (c)(1),
(2), (4) Date: Jul. 20, 2001
(87) PCT Pub. No.: WO00/43761
PCT Pub. Date: Jul. 27, 2000

(30) Foreign Application Priority Data

Jan. 23, 1999 (DE) .......................................... 199 02 617
May 8, 1999 (DE) .......................................... 199 21 317

(51) Int. Cl.[7] .............................................. G01B 15/02
(52) U.S. Cl. .......................................... 378/90; 378/46
(58) Field of Search ........................... 378/44, 45, 47, 378/48, 49, 86, 88, 90, 46

(56) References Cited

U.S. PATENT DOCUMENTS 6,118,850 A * 10/2000 Mayo et al. ................... 378/83
6,266,390 B1 * 7/2001 Sommer, Jr. et al. ......... 378/45
6,285,734 B1 * 10/2001 von Alfthan ................... 378/46

FOREIGN PATENT DOCUMENTS

JP        401105146 A  *  9/1989  ................. 378/44

OTHER PUBLICATIONS

Gigante G E Et Al: "Analysis of metal alloys by Rayleigh to Compton ratios and X–ray fluorescence peaks in the 50 to 122 keV energy range" Nuclear Instruments & Methods in Physics Research, Section B (Beam Interactions with Materials and Atoms), Sep. 1985, Netherlands, Bd. B12, Nr. 2, Seiten 229–234, XP002147026 ISSN: 0168–583X.

H Kunzendorff: "Quik determination of the average atomic number Z by X–ray scattering." Nuclear Instruments and Methods., Bd. 99, 1972, Seiten 611–612, XP002147027 North–Holland Publishing Company. Amsterdam., NL in der Anmeldung erwaehnt.

* cited by examiner

*Primary Examiner*—David P. Porta
*Assistant Examiner*—Elizabeth Gemmell
(74) *Attorney, Agent, or Firm*—Millen, White, Zelano & Branigan, P.C.

(57) ABSTRACT

The invention relates to a method for classifying and identifying by means of energy dispersion X-ray fluorescence analysis chemical substances whose X-ray fluorescence lines cannot be detected and which therefore cannot be classified by energy dispersion X-ray fluorescence analysis alone. Said method is characterized in that the sample to be analyzed is analyzed in its original packaging or natural state without prior processing in a sample vessel. According to the method the sample is: a) positioned in front of the measuring aperture in a sample chamber of an X-ray fluorescence apparatus; b) measured; and c) classified and identified by application of multivariate, statistical techniques to the measurement signals obtained, i.e., to the Compton and Rayleigh scattering.

11 Claims, 10 Drawing Sheets

ENERGY DISPERSION X-RAY FLUORESCENCE ANALYSIS OF CHEMICAL SUBTANCES

The present invention relates to the discrimination and classification, by means of X-ray fluorescence analysis, of chemical substances whose X-ray fluorescence lines cannot be detected and which therefore cannot be classified by energy dispersive X-ray fluorescence analysis (EDXRFA) alone, through the packaging and without having to take a sample.

A fast check of the identity of laboratory chemicals is necessary in many situations. This is primarily true in chemical companies within the context of so-called returned material stream management. In this case, returned material stream means chemicals which are taken back after having been returned to the chemical works by end-users or wholesalers.

Under the circular economy law, every returned material stream is to be regarded as waste until a control procedure has plausibly characterized every returned material stream. Only then can the returned material stream be categorized as a product, or raw material, secondary raw material or definitively as waste.

After the chemicals have been taken back, they are correspondingly documented, inspected in terms of their composition and then re-used as secondary raw materials in production where appropriate.

Energy dispersive X-ray fluorescence analysis (EDXRFA) is a fast analysis method for qualitative and quantitative determination of elements in substances. The determination is carried out via evaluation of the X-ray fluorescence lines. The X-ray fluorescence lines of elements with atomic numbers between 21 and 92 can be detected through a PE (polyethylene) container and allocated. However, elements with atomic numbers between 1 and 20 make up a large proportion of substances. It is not possible to characterize these elements, and therefore these substances, using conventional EDXRFA evaluation (X-ray fluorescence line determination and evaluation) owing to the lack of X-ray fluorescence lines.

Information about the substance and its composition can be obtained via the coherent (Rayleigh scattering) and incoherent (Compton scattering) scattering of X-rays in the substance. Correlations between the average atomic number and the ratio between coherent and incoherent scattered radiation are known, and are described for example by H. Kunzendorf in Nuclear Instruments and methods, 99 (1972) 611–612. The matrix correction, based on inelastic scattered radiation, for X-ray fluorescence lines is used by various EDXRFA suppliers for quantative evaluation.

It is therefore an object of the present invention to characterize and discriminate from one another, without risk and without other additional analysis methods and without having to take a sample, substances whose X-ray fluorescence lines cannot be detected and which therefore cannot be classified by energy dispersive X-ray fluorescence analysis (EDXRFA) alone.

It has now been found, surprisingly, that it is also in fact possible to employ energy dispersive X-ray fluorescence analysis for classifying and identifying chemical substances with atomic numbers 1 to 20, specifically by the application of multivariate statistical methods to the measurement signals obtained for the entire Compton and Rayleigh scattering range.

Previously, these substances whose X-ray fluorescence lines cannot be detected, but which only have a Compton and Rayleigh scattering range, could not be discriminated from one another but were instead assigned together to an allocation field. If it was desired to ascertain more accurately which individual elements or substances were present, it was necessary to carry out other conventional analyses.

The invention therefore relates to a method for classifying and identifying, by means of energy dispersive X-ray fluorescence analysis, chemical substances whose X-ray fluorescence lines cannot be detected and which therefore cannot be classified by energy dispersive X-ray fluorescence analysis (EDXRFA) alone, which is characterized in that the sample to be analysed is a) positioned in front of the measurement opening in a sample chamber in an X-ray fluorescence system, then measured, and b) classified and identified by application of multivariate statistical methods to the measurement signals obtained, i.e. for the Compton and Rayleigh scattering range, in its original packaging or per se without prior processing in a sample vessel.

As multivariate statistical methods, principal component analysis (PCA) is applied for detecting differences of the substances and/or regularized discriminance analysis (RDA) is applied for discriminating and classifying the substances.

As already mentioned, checking the identity of laboratory chemicals is particularly important when chemicals are taken back. As statistics show, it is primarily small packagings which are sent back in large quantities to chemical plants. Substances in small packagings are therefore often documented and analysed in small-packaging sorting systems (SSS). In the case of analysing different substance streams, each individual substance needs to be analysed in its packaging. Opening the packaging and taking a sample must not be performed in the room where the sorting system is and the analyses are carried out, because of the risk to people and the environment which should be avoided when dealing with old chemicals (Circular economy law and waste avoidance law (Krw-/AbfG) 1994 (BGBl. I, 1354); regulation No. 259/93 of the council for monitoring and control of the movement of waste in, into and out of the European Community 1993 (ABl. L 30, 1); regulation governing the introduction of the European waste catalogue (EAK regulation) 1996 (BGBl. I, 1428); regulation governing the determination of waste requiring special monitoring (BestbüAbfV) 1996 (BGBl. I 1366); regulation governing the determination of recyclable waste requiring special monitoring (BestbüAbfV) 1996 (BGBl. I 1377); second general administrative order concerning the waste law (TA Abfall) 1991 (GMBl. p. 139, corr. 496); regulation governing the protection of hazardous substances (GefStoffV) 1993 (BGBl. I 1782)). Energy dispersive X-ray fluorescence analysis (EDXRFA) has crystallized as a suitable method for analysis through unopened packaging.

The analysis is hence preferably carried out through the packaging, in which case a variety of packaging materials (glass or polyethylene packaging) may be present and need to be taken into consideration correspondingly during the allocation.

When inspecting these substances, complete identification of the substances including information about the main and subsidiary constituents is not required. Plausible allocation of the substance spectrum recorded through the packaging to the spectrum of the substance name written on the packaging label is, however, expected. This type of analysis is referred to as allocation analysis.

Substances which contain elements with an atomic number (AN)>22 (Ti) can, depending on the packaging size, be characterized through PE packaging with the aid of their element lines. The peak detection, peak parameter determination (peak position, width at half maximum and area) as well as the subsequent checking of the XRFA data against the information in the database, take place automatically. A further innovation is that these substance groups can also be discriminated substantially better using multivariate statistical methods. To that end, the X-ray fluorescence range of the element with an AN>22 and the Compton and Rayleigh scattering range are calculated using the multivariate statistical methods.

As already mentioned, however, elements with atomic numbers between 1 and 20, which do not have detectable X-ray fluorescence lines, make up a large proportion of substances. It is not possible to characterize these elements, and therefore the substance (e.g. between NaCl and NaCN or $K_2CO_3$ and KF), using conventional EDXRFA evaluation owing to the lack of X-ray fluorescence lines. The XRFA measurement of such substances only provides scattered-radiation spectra which do not permit evaluation with conventional EDXRFA evaluation. These substances have therefore previously been assigned to a common "allocation field".

This means, however, that only very rough assignment can take place here. For more accurate classification, other analysis methods must be employed in these cases, sometimes with prior sampling and processing of the sample. These further examinations are, however, time-consuming and expensive. These additional analyses can now be avoided through the present invention.

According to the invention, further discrimination by the application of multivariate statistical methods to the Compton and Rayleigh scattering range can now be carried out for these substances, within the allocation field which is defined with conventional X-ray fluorescence (XRFA) evaluation.

Principal component analysis (PCA) and regularized discriminance analysis (RDA) methods are preferred as multivariate statistical methods for this. These methods are known per se to the person skilled in the art, and are dealt with at length in many literature references (an example citation for RDA is: J. H. Friedman, J. Amer. Statistical Association, 1989, Vol. 84, No. 405, 165–175).

By the direct application of multivariate statistical methods to the Compton and Rayleigh scattering range, further allocation can be carried out. According to the invention, the different methods can respectively be applied individually to the scattering spectra, or alternatively both in succession.

With the aid of principal component analysis, further subclasses become detectable in the classes defined by the conventional XRFA evaluation. With PCA, spectral differences of the individual substances can be made visible in the PCA representation. In Example 1 (FIG. 1), the result of the PCA evaluation is represented in the form of a "score plot". Here, the scattered-radiation range of 20 substances (in a PE sample vessel), which do not give X-ray fluorescence signals, was calculated by principal component analysis.

With discriminance analysis methods, mathematical models are set up for the substance classes—substances can subsequently be allocated to a class using these models.

Classes of recorded spectra of different substances are visualised using PCA, then their classes are calculated using RDA. This means that both the spectral range, or the principal components calculated for the spectral range, can be used as variables in the RDA. The number of principal components used is determined using the so-called "eigen value 1 criterion" or by cross-validation.

The individual steps from the spectrum recording to the classification are described below.

The sample to be analysed is firstly positioned in front of the measurement opening in a sample chamber in the X-ray fluorescence system, in its original packaging—it is hence unnecessary to open the packaging and sampling is superfluous—or per se without prior processing in a sample vessel.

The packaging or the sample vessel containing the sample to be analysed may consist of a material selected from the group polyethylene, glass, aluminium, paper and cardboard.

The EDXRFA spectrum is now recorded. Then, if X-ray fluorescence lines of the elements in the substance are not present, the Compton and Rayleigh scattering range from 19.6 to 26.3 keV (note: this range only applies to excitation using an Ag tube, see Table 1; when other excitation sources are used, the scattering range lies in a range corresponding to the excitation source) is sought for the multivariate statistical calculations (PCA, RDA). Next—if desired—the principal components are calculated using PCA for the new substance in the new model (inc. substance) which contains the spectrum of the substance. This step is optional.

In the next step, the classes are compiled and defined in RDA with a learning data record (spectral ranges or optionally the principal components identified in the previous step).

This is followed by classification/assignment of the new substance (test data record, i.e. spectral range or principal components) to a class from the learning data record (optionally, the principal components from the PCA can also be employed for the classification, instead of the spectrum). The learning data record must naturally contain the target class. The classification is carried out using the calculations described in the literature. The following literature references may be cited as examples for this:

Friedman, J. H., "Regularized Discriminant Analysis" in J. Am. Stat. Assoc. (1989) 84, 165–175; Frank, I. E., Friedman, J. H., Classification: "oldtimers and newcomers" in J. Chemom. (1989) 33, 463–75; Wu, W., Mallet, Y., Walczak, B., Penninckx, W., Massart, D. L., Heuerding, S., Erni, F., "Comparison of regularized discriminant analysis, linear discriminant analysis and quadratic discriminant analysis, applied to NIR data" in Anal. Chim. Acta (1996) 3293, 257–265; Baldovin, A., Wen, W., Massart, D. L., Turello, A. "Regularized discriminant analysis RDA—Modeling for the binary discrimination between pollution types" in Chemom. Intell. Lab. Syst. (1997) 381, 25–37.

The last step involves comparison between the class allocated to the spectrum and the actual class, or the substance name written on the label. If the result matches, the substance is processed further by being stored or used in production.

All this evaluation is preferably carried out automatically by applying correspondingly tailored software, which substantially accelerates the entire analysis duration and calculation time. The PCA and RDA algorithm is commercially available and can be implemented in the subsequent evaluation data processing.

The substances to be analysed, in their packaging, normally reach the EDXRFA system on a conveyor belt. The positioning of the packaging in front of the measurement opening, the recording of the EDXRFA spectrum, the evaluation of the spectra, the subsequent spectrum allocation and the repositioning of the packaging on the conveyor belt are carried out fully automatically. Accordingly, the EDXRFA system and the associated components (sample chamber, interfaces with the substance database, EDXRFA control) must be configured so that automatic operation of the individual components is possible.

The invention therefore also relates to the use of the method within an automated system for sorting and allocating old or new packagings which contain chemical substances.

The automated system preferably consists of the following components or steps:
- conveyor belt for the substances to be analysed in their packaging;
- EDXRFA system;
- positioning the packaging in front of the measurement opening in a sample chamber, the sample chamber fully enclosing the packaging;
- measurement;
- spectrum evaluation and allocation;
- further evaluation by application of multivariate statistical methods, and
- repeated, more accurate allocation;
- repositioning the packaging on the conveyor belt.

Preferably, an X-ray fluorescence analysis apparatus, consisting of an X-ray tube, a generator, an energy-resolving detector and evaluation electronics, is used.

In a preferred embodiment, the following configuration of the EDXRFA system is selected: X-ray tube with generator and semiconductor detector, the measurement geometry, i.e. the angle between the excitation source, the sample and the detector, is selected variably between 45° and 90°, so that the Compton and Rayleigh scattering lines are resolved in the detector.

The sample chamber must fully enclose the packaging since, when dealing with ionizing radiation, it is necessary to comply with protective mechanisms according to the X-ray regulation. It is necessary to ensure that the emerging X-radiation does not exceed a defined limit value. The sample chamber is preferably made of a material which does not increase the spectrum background (scattering) in the sample chamber, is automatically openable and closable, and is adaptable to the EDXRFA apparatus.

The parameters for routine operation, i.e. the X-ray tube voltage and current, the primary beam filter material and thickness, the detector diaphragm aperture, the positional coordinates for the packaging in front of the EDXRFA measurement opening, can be experimentally determined and adjusted as desired and according to requirements. For subsequent allocation of the spectra to the substances, the packaging sizes and materials and the packaging positions should also respectively be taken into account.

Since it is necessary to cope with a large number of packages being taken back, the analysis duration should be of short length. According to the invention, the measurement time for recording the spectra is preferably $\leq 30$ seconds.

Example A, Table 1 describes a preferred configuration with the parameters for measurement and evaluation. This list is intended merely as an entirely non-limiting example. Example A also lists the preferred general measurement conditions for the trials.

Diagram 1 shows the EDXRFA measurement geometry and coordinate system for the packaging positioning for a preferred embodiment according to the invention.

The method according to the invention provides a fast, reliable and effective analysis method for identifying chemical substances through the packaging. EDXRFA is in principle extended to those substances comprising elements with atomic numbers between 1 and 20 which could not previously be discriminated in this way. Substantially improved characterization and allocation can therefore be achieved when taking back chemicals, without having to employ other analysis methods with laborious sample processing and sampling.

Even without further embodiments, it is assumed that a person skilled in the art can use the above description in a very wide scope. The preferred embodiments should therefore merely be regarded as descriptive disclosure which is by no means limiting in any way.

The complete disclosures of all applications and publications cited above and below are incorporated in this application by reference.

The following examples are only intended to explain the invention further.

EXAMPLE A

Table 1 describes the configuration, with the parameters for measurement and evaluation, which was employed in the following examples.

TABLE 1

EDXRFA system equipment for waste-specific allocation when taking back substances

| Model | Description |
|---|---|
| FK 60-20 | Fine focus tube with Ag anticathode, 60 kV, 60 mA |
| GI-XRF02 | Adjustable-level instrument including screening and safety devices for holding the Si(Li) semiconductor detector, collimator and the tube protective cap |
| C-42865 | Si(Li) semiconductor detector, active area: 80 mm$^2$, resolution: $\leq$ 165 eV for 5.9 keV at 2000 pulses/s, preamplifier with FET input stage, pulsed optoelectronic feedback, immersion cryostat with 25 $\mu$m Be input window, 30 l liquid-gas container |
| RS-3001 | X-ray generator, tube cap with a window, 5 m HV cable, adapter and tube cap frame |
| RACK-300 | Analogue electronics in 19" rack with analogue power pack, active-filter amplifier with triangle pulse shaping, baseline restorer, pulse pileup rejecter and pulse spreader, high-voltage detector supply, continuously adjustable from 0–1000 V |
| TSI-MCA | Analogue/digital converter and pulse level analyser for ISA bus |
| TSI-AQL | Program package for EDXRFA under MS Windows ™ |
| ICP-300A | Industry PC in 19" case with 250 W power pack, auxiliary fan, passive bus board with 8 ISA, 2 ISA/PCI and 4 PCI ports, single-board computer with Pentium/133 CPU, 256 kB cache, 32 MB RAM, 2 × ser., 1 × par. interface E-IDE interface, 1.44 MB floppy disk drive, 1.2 GB hard disk, CD-ROM drive, Matrox-Millennium PCI graphics card (2 MB), MF keyboard, MS mouse, MS DOS 6.22 and MS Windows 3.11 ™ |
| EIZO-57S | SVGA colour video monitor with 43.2 cm (17") format CRT, TOC 95 model Eizo Flexscan T57S Device cabinet in 19" standard for holding the X-ray generator, the system electronics and the industry PC Primary beam collimator (3 mm beam diameter, material: Al) Primary beam filter (materials Cu, Mo, Ag) |
| WECO KL 04 | Circulation cooler (from GWK) |
| SCAN for Windows ®, Version 1.1 | Software package for chemometric classification of substances, from Minitab |

The measurement conditions for the substance classification trials may be selected as follows:

| | |
|---|---|
| Tube high voltage | 45 kv |
| Tube current | 4 mA |
| Primary beam collimator diameter | 2 mm |

| -continued | |
|---|---|
| Primary beam filter material | Ag |
| Primary beam filter thickness | 0.12 mm |
| Detector diaphragm material | Al |
| Detector diaphragm aperture | 3 mm |
| Detector time constant | 2 µs |
| Height X-ray beam - packaging bottom | 1.5 cm |
| Measurement time for the classification trials | 20 s |
| Packaging position in front of the EDXRFA measurement opening | 10/0 (in mm, right of detector centre) |
| Angle (primary beam - sample - detector) | ca. 60° |

EXAMPLE 1

The measurement parameters and conditions can be found in Example A.

1.1

The Compton and Rayleigh scattered-radiation range (19.7–26.2 keV) of 20 substances, which do not give an X-ray fluorescence signal, are calculated using principal component analysis (PCA). FIG. 1 represents the result of the PCA evaluation in the form of a "score plot".

1.2

The results of the RDA (regularized discriminance analysis) calculation for the 20 substances measured in 1.1 are represented in FIG. 2 (calculated with the Compton and Rayleigh scattering range) and in FIG. 3 (calculated with the first three principal components from the PCA).

1.3

Table 2 lists the various substances from this measurement series with their physical data.

TABLE 2

Various substances and their physical data from the no-element group (measurement series 1)

| Substance | M/g/mol | Average AN | Density/g/cm³ |
|---|---|---|---|
| $(NH_4)_2CO_3$ | 96.09 | 6.869 | 1.6 |
| $(NH_4)_2SO_4$ | 132.14 | 9.301 | 1.766 |
| $NH_4Cl$ | 53.49 | 13.176 | 1.531 |
| $H_3BO_3$ | 61.83 | 7.133 | 1.435 |
| $BeSO_4 \times 4H_2O$ | 177.14 | 8.925 | 1.713 |
| $Na_2CO_3$ | 105.99 | 9.075 | 2.533 |
| $Na_2SO_4$ | 142.04 | 10.777 | 2.698 |
| NaCN | 49.01 | 8.631 | 1.546 |
| NaF | 41.99 | 10.095 | 2.79 |
| NaCl | 58.44 | 14.641 | 2.163 |
| $MgSO_4 \times 7H_2O$ | 246.48 | 9.034 | 1.68 |
| $MgCl_2 \times 6H_2O$ | 203.31 | 11.201 | 1.57 |
| $K_2CO_3$ | 138.21 | 14.049 | 2.428 |
| $K_2SO_4$ | 174.27 | 14.407 | 2.662 |
| KCN | 65.12 | 14.020 | 1.56 |
| KF | 58.1 | 15.729 | 2.49 |
| KCl | 74.56 | 18.047 | 1.984 |
| $CaCl_2 \times 2H_2O$ | 147.02 | 15.420 | 1.85 |
| $CaSO_4 \times 2H_2O$ | 172.17 | 12.119 | 2.32 |
| $CaCO_3$ | 100.09 | 12.565 | 2.95 |

EXAMPLE 2

The measurement parameters and conditions can be found in Example A.

2.1

In this example, 5 chromium compounds were studied. Both the element-line and the Compton and Rayleigh scattering ranges were evaluated using principal component analysis (PCA). FIG. 4 represents the result of the PCA evaluation in the form of a "score plot".

2.2

The results of the RDA (regularized discriminance analysis) calculation for this test series (see section 1.2) are represented in FIGS. 5 and 6.

2.3

Table 3 lists the studied substances from the chromium group and their physical data.

TABLE 3

Studied substances from the chromium group and their physical data (measurement series 2)

| Substance | M/g/mol | Average AN | Density/g/cm³ |
|---|---|---|---|
| $(NH_4)_2CrO_4$ | 152.07 | 12.153 | 1.86 |
| $K_2CrO_7$ | 294.19 | 16.579 | 2.69 |
| $KCr(SO_4)_2 \times 12H_2O$ | 499.41 | 11.215 | 1.83 |
| $Cr_2O_3$ | 151.99 | 18.947 | 5.21 |
| $CrCl_3 \times 6H_2O$ | 266.45 | 14.397 | 2.76 |

EXAMPLE 3

3.1

Measurement series 3 was carried out with substances from the iron group using the measurement parameters and conditions described in Example A.

Seven iron compounds were studied in this example. Both the element-line and the Compton and Rayleigh scattering ranges were evaluated using principal component analysis (PCA). FIG. 7 represents the result of the PCA evaluation in the form of a "score plot".

3.2

The results of the RDA (regularized discriminance analysis) calculation for this test series (see section 1.2) are represented in FIGS. 8 and 9.

3.3

Table 4 shows the physical data of this test series.

TABLE 4

Studied substances from the iron group and their physical data (measurement series 3)

| Substance | M/g/mol | Average AN | Density /g/cm³ |
|---|---|---|---|
| $FeSO_4 \times 7H_2O$ | 278.02 | 12.183 | 1.89 |
| $(NH_4)_2Fe(SO_4)_2 \times 6H_2O$ | 392.14 | 11.440 | 1.86 |
| $K_4[Fe(CN)_6] \times 3H_2O$ | 422.39 | 13.812 | 1.85 |
| $K_3[Fe(CN)_6]$ | 329.26 | 14.279 | 1.894 |
| $FeCl_3 \times 6H_2O$ | 270.3 | 14.947 | 2.804 |
| $Fe_2O_3$ | 159.69 | 20.591 | 5.52 |
| Fe | 55.85 | 26 | 7.87 |

The examples with the PCA calculations show that, in the novel data space which is spanned by the principal components, 20 substances from the no-element group and selected substances from the chromium and iron one-element groups can be separated from one another. This separation is not achieved with conventional EDXRFA evaluation of the spectra recorded through the packaging.

The best possible separation of the substances in the novel data space, and the smallest scatter within the groups, is achieved for the no-element group by PCA calculation when taking the Compton and Rayleigh scattering range into account. For the one-element groups, good separation of the groups from one another and small scatter within the groups is achieved by PCA calculation using a combination of the fluorescence-line range of the element and the Compton and Rayleigh scattering range.

The examples with RDA calculations show that EDXRFA spectra recorded through the packaging can be discriminated from one another, with the aid of the relevant RDA model, if the spectra for the RDA have detectable spectral similarities. For the chromium and iron one-element groups, it is possible to allocate the substances to a previously defined class both using the spectral range (fluorescence-line, Compton and Rayleigh scattering range) and using the significant PCs from the PCA as variables. For the iron group, classification using the spectral range is actually better (calculated by internal cross-validation of the iron data record).

The RDA classification of the substances of the no-element group to their classes functions similarly.

Figure 1:
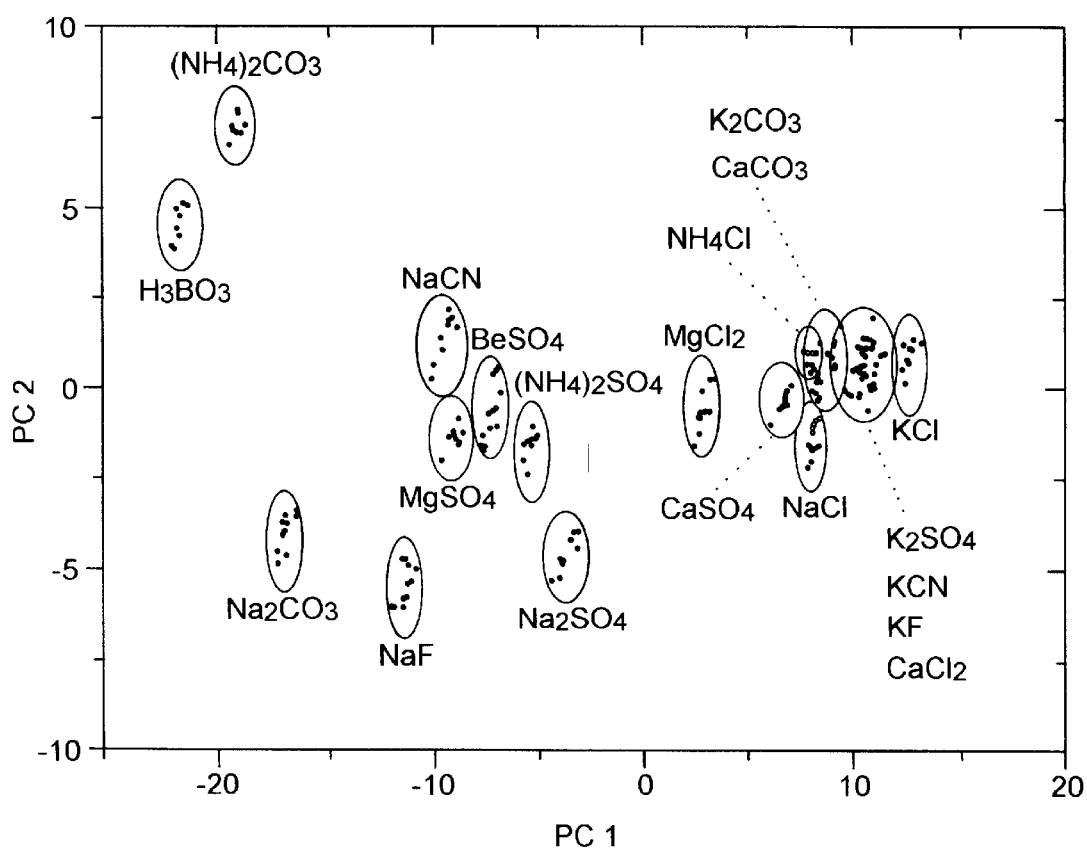
FIG. 1 shows a score plot of 20 substances, measured in the same PE container (white, 80 ml), spectrum detail: Compton and Rayleigh scattering range, measurement time: 20 s, PC: principal component.
Figure 2:
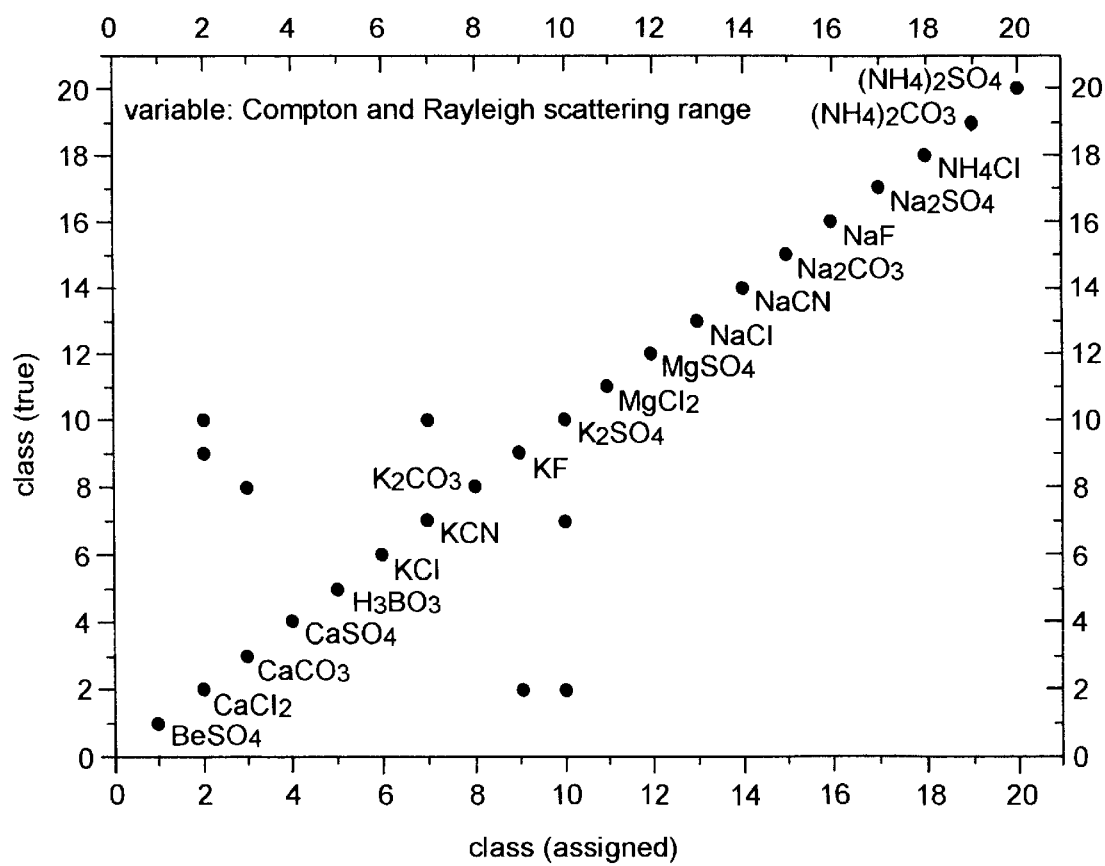
FIG. 2 shows a graphical representation of the RDA results of 20 substances (20 classes) of the test data record in Table 2, calculated using the SCAN for Windows® software, measurement time: 20 s, variables: Compton and Rayleigh scattering range.
Figure 3:
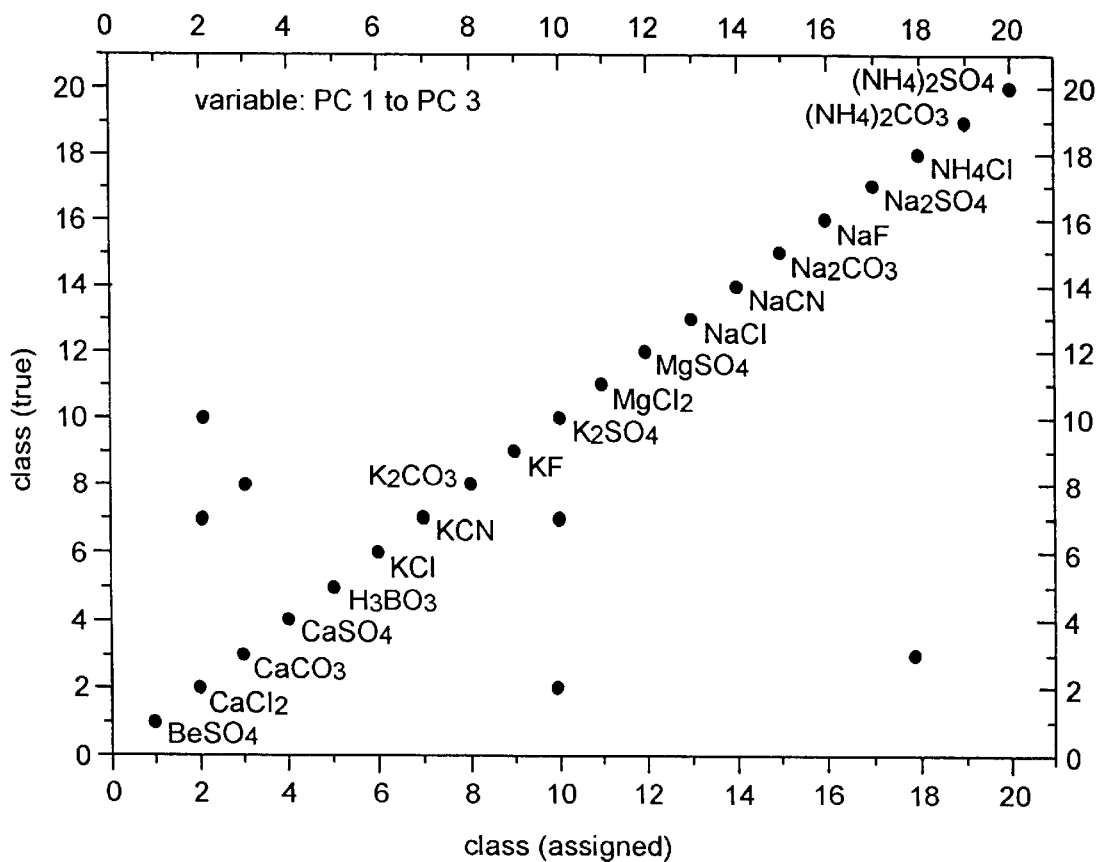
FIG. 3 shows a graphical representation of the RDA results of 20 substances (20 classes) of the test data record in Table 2, calculated using the SCAN for Windows® software, measurement time: 20 s, variables: PC 1 to PC 3.
Figure 4:
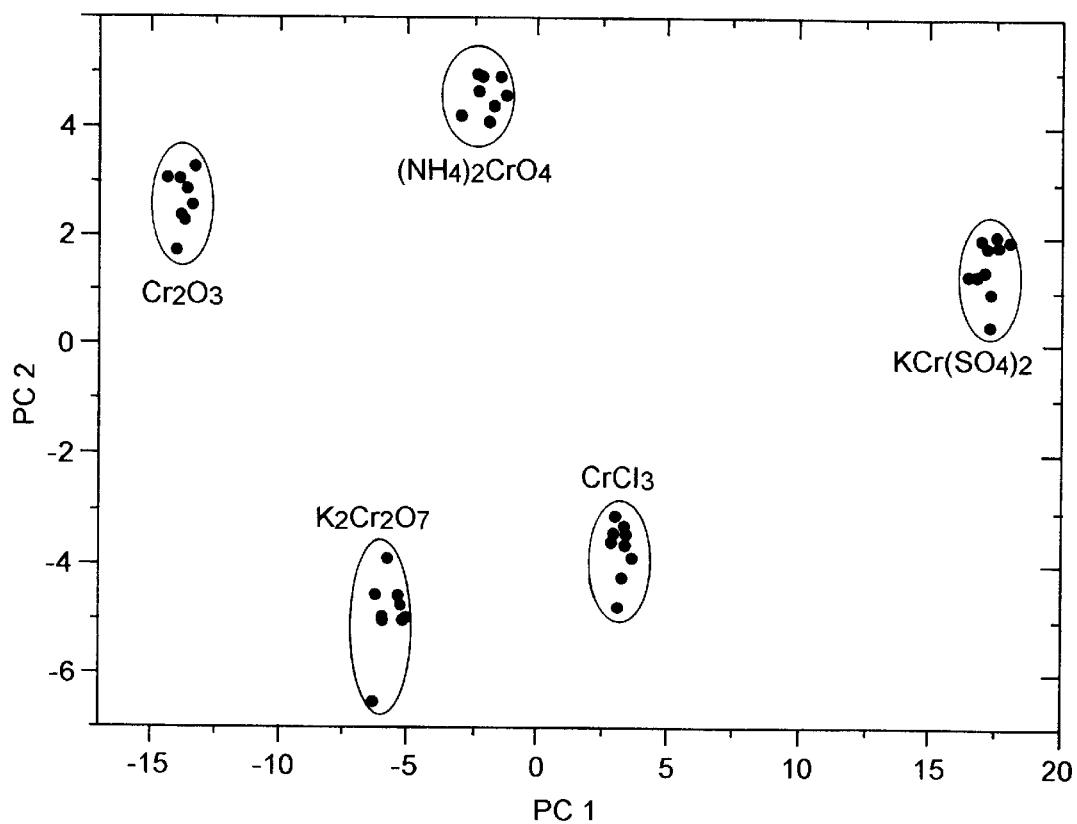
FIG. 4 shows a score plot of the 5 Cr compounds, element-line and Compton and Rayleigh scattering range, measurement time: 20 s.
Figure 5:
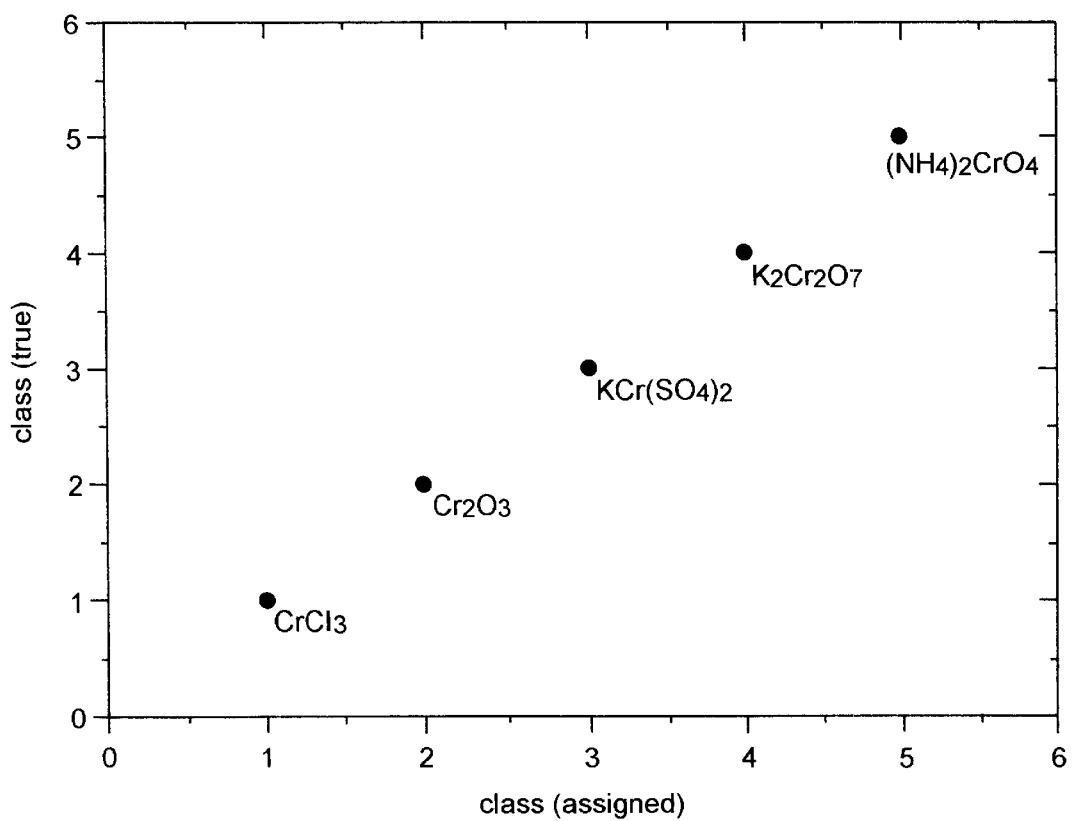
FIG. 5 shows a graphical representation of the RDA results of the five chromium compounds (5 classes) in Table 3 (classification check using cross-validation), calculated using the SCAN for Windows® software, measurement time: 20 s, variables: spectral ranges.
Figure 6:
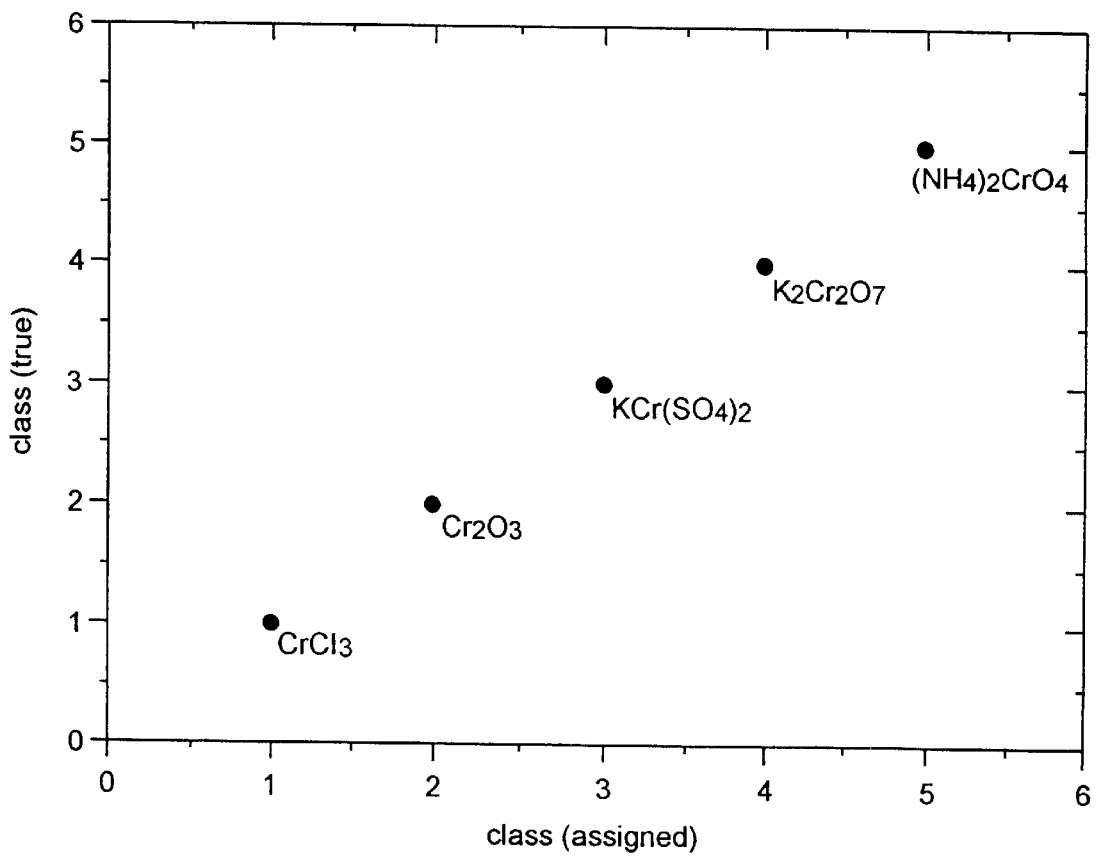
FIG. 6 shows a graphical representation of the RDA results of the five chromium compounds (5 classes) in Table 3 (classification check using cross-validation), calculated using the SCAN for Windows® software, measurement time: 20 s, variables: PC 1 to PC 3.
Figure 7:
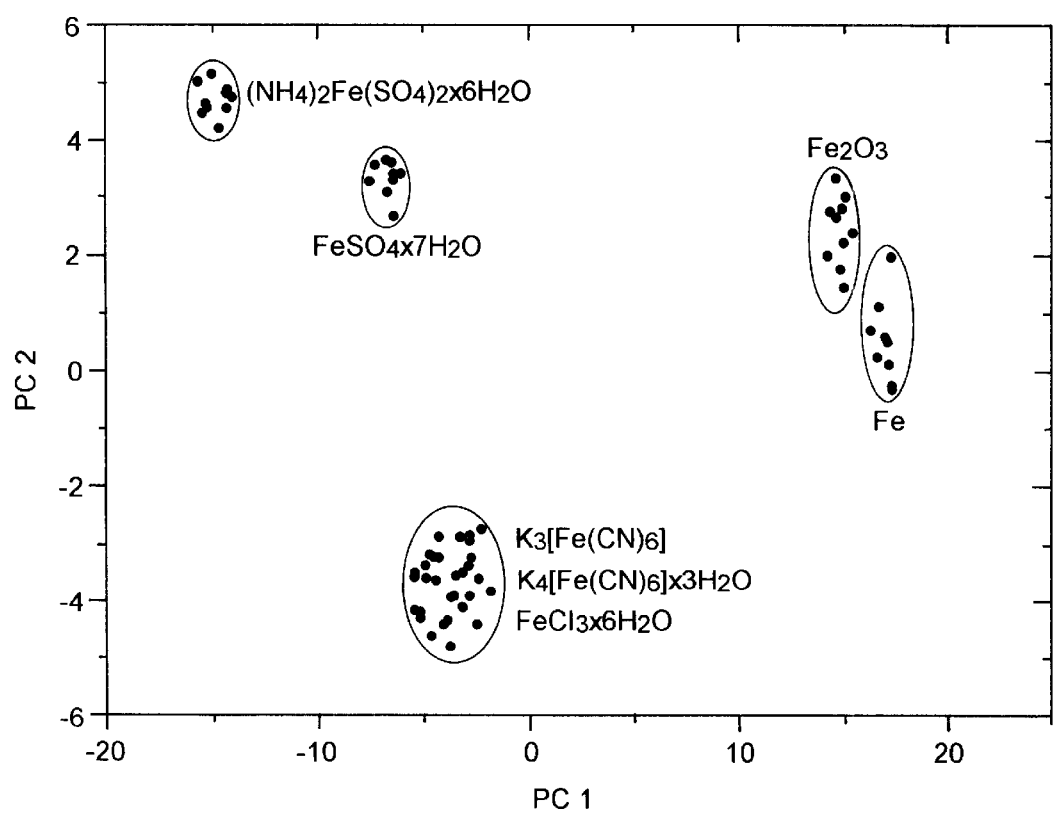
FIG. 7 shows a score plot of the 7 Fe compounds, element-line and Compton and Rayleigh scattering range, measurement time: 20 s.
Figure 8:
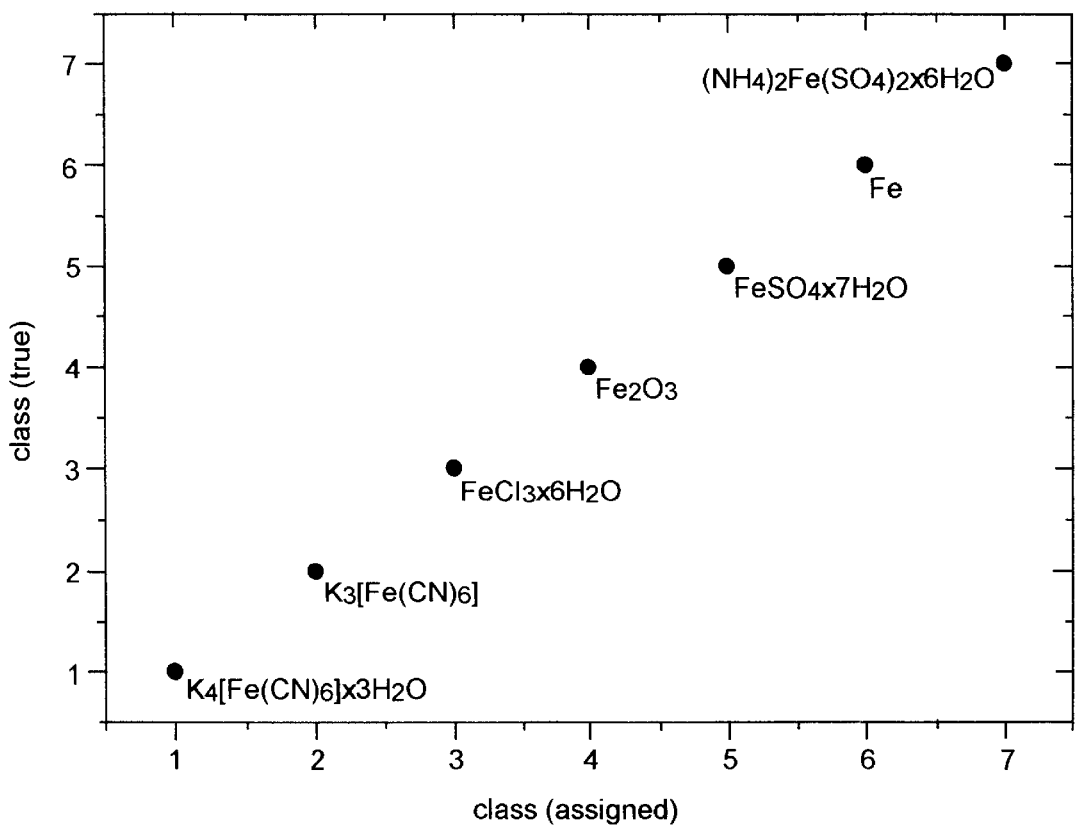
FIG. 8 shows a graphical representation of the RDA results of the seven iron compounds (7 classes) in Table 4 (classification check using cross-validation), calculated using the SCAN for Windows® software, measurement time: 20 s, variables: spectral ranges.
Figure 9:
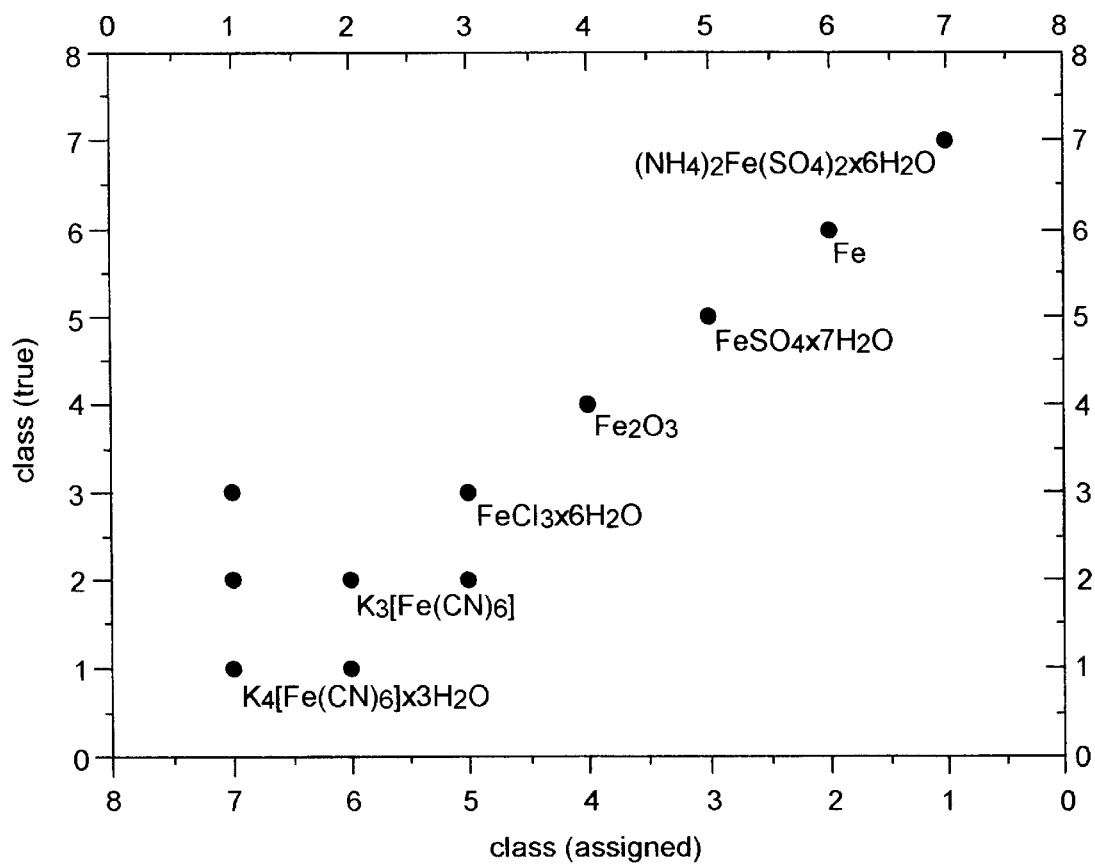
FIG. 9 shows a graphical representation of the RDA results of the seven iron compounds (7 classes) in Table 4 (classification check using cross-validation), calculated using the SCAN for Windows® software, measurement time: 20 s, variables: PC 1 to PC 3.
Figure 10:
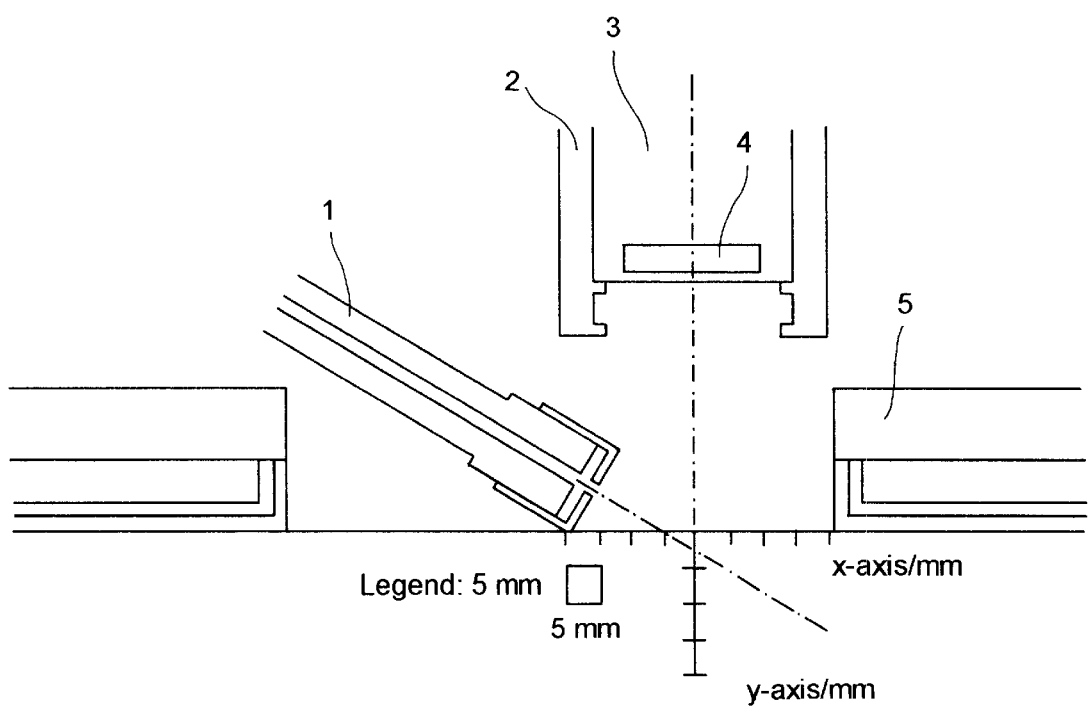
FIG. 10 shows an examples of a system for carrying out the method of the invention. The system includes (1) a primary beam collimator with filter frame (material: Al), (2) a detector diaphragm frame (material: Al), (3) a detector, (4) a Si(Li) crystal and (5) a EDXFRA aperture casing (material: Al, 10 mm).

What is claimed is:

1. A method for classifying and identifying, by means of energy dispersive X-ray fluorescence analysis, chemical substances whose X-ray fluorescence lines cannot be detected and which therefore cannot be classified by energy dispersive X-ray fluorescence analysis (EDXRFA) alone, which comprises:

a) positioning a sample to be analyzed in front of a measurement opening in a sample chamber in an X-ray fluorescence system, b) measuring the scattering of X-rays signals from the sample, and c) classifying and identifying the chemical substances, whose X-ray fluorescence lines cannot be detected, by application of principal component analysis (PCA) and/or regularized discriminance analysis (RDA) methods to the X-ray Compton and Rayleigh scattering spectral ranges of the measured signals in b), wherein the sample is maintained in its original packaging or is otherwise analyzed without prior processing in a sample vessel.

2. The method of claim 1, wherein, when positioning the sample to be analyzed, the angle between the excitation source, the sample and the detector, also referred to as the measurement geometry, is selected variably between 45° and 90°, so that the Compton and Rayleigh scattering lines are resolved in the detector.

3. The method of claim 1, wherein the sample to be analysed is measured and classified in its closed original packaging.

4. The method of claim 3, wherein the original packaging of the sample and/or the sample vessel comprises a material selected from the group consisting of polyethylene, glass, aluminum, paper and cardboard.

5. The method of claim 1, wherein the spectral differences of the individual substances are made visible in the PCA representation by the application of principal component analysis.

6. The method of claim 1 wherein the classification/identification of the sample is carried out by application of regularized discriminance analysis (RDA) such that substance identification is made by direct calculation of a spectrum or spectral range, the test substance then being allocated to a previously determined and defined class.

7. The method of claim 1, wherein the RDA method is applied, for classification/identification, to the principal components obtained by PCA.

8. The method of claim 1, wherein an X-ray fluorescence analysis apparatus, comprises of an X-ray tube, a generator, an energy-resolving detector and evaluation electronics, is used to carry out the method.

9. The method of claim 1, wherein the measurement time for recording the spectrum of a sample is $\leq 30$ seconds.

10. The method of claim 1, wherein the method is conducted within an automated system for sorting and allocating old or new packagings which contain chemical substances.

11. The method of claim 10, wherein the automated system comprises the following components or steps:

conveying on a conveyor belt the substances to be analysed in their packaging;

an EDXRFA system;

positioning the packaging in front of the measurement opening in a sample chamber, the sample chamber fully enclosing the packaging;

measuring the X-ray spectrum;

evaluating the spectrum and making an allocation;

further evaluating by application of multivariate statistical methods, and repeated, more accurate allocation;

repositioning the packaging on the conveyor belt.

* * * * *

UNITED STATES PATENT AND TRADEMARK OFFICE
CERTIFICATE OF CORRECTION

PATENT NO.     : 6,496,562 B1
DATED          : December 17, 2002
INVENTOR(S)    : Henrich et al.

It is certified that error appears in the above-identified patent and that said Letters Patent is hereby corrected as shown below:

<u>Title page, Item [54] and Column 1, line 3,</u>
Change "SUBTANCES" to -- SUBSTANCES --.

<u>Column 10,</u>
Line 47, change "$\leqq$" to -- $\leq$ --.

Signed and Sealed this

First Day of July, 2003

JAMES E. ROGAN
*Director of the United States Patent and Trademark Office*